United States Patent [19]

Clusener

[11] Patent Number: 4,618,274
[45] Date of Patent: Oct. 21, 1986

[54] DILATOMETER HOUSING

[76] Inventor: Gerhard R. Clusener, 112 Reni Rd., Manhasset, N.Y. 11030

[21] Appl. No.: 600,892

[22] Filed: Apr. 16, 1984

[51] Int. Cl.[4] .................. G01K 1/08; G01N 25/00
[52] U.S. Cl. .................................. 374/208; 374/55
[58] Field of Search ............... 374/55, 56, 210, 208; 206/829; 33/125 B, 172 E

[56] References Cited

U.S. PATENT DOCUMENTS

| 3,680,357 | 8/1972 | Clusener | 374/56 |
| 3,748,892 | 7/1973 | McKendree, Jr. et al. | 374/56 |
| 3,805,589 | 4/1974 | Clusener et al. | 374/56 |
| 3,885,416 | 5/1975 | Cooper | 374/56 |
| 3,898,836 | 8/1975 | Clusener | 374/56 |
| 4,069,703 | 1/1978 | Standish et al. | 374/56 |

FOREIGN PATENT DOCUMENTS 2307267 11/1976 France ................... 374/55

Primary Examiner—Charles Frankfort
Assistant Examiner—W. Morris Worth
Attorney, Agent, or Firm—Burton E. Levin

[57] ABSTRACT

Dilatometers in which the dilation sensor, pushrod or rods and the specimen holder all are enclosed within a unitary hermetically sealed housing, including an elongated protective tube for the portion of the specimen holder that is inserted in an electric tube furnace. The housing, which is compact and can be evacuated and flushed with an inert or reducing gas to protect its contents from oxidation, can easily and quickly be withdrawn as a unit from a stationary or unopened furnace to facilitate the rapid installation of similar housings having specialized sensors or tubular enclosures designed for different applications. The sensor, push rod and specimen holder also can be readily removed as a unit from the housing, which permits rapid specimen changes without the necessity of withdrawing the protective tube from the furnace or realigning it after reinsertion. A dilation sensor also is described which utilizes a calibrating micrometer positioned abreast of a linear variable differential transformer. This compact design minimizes temperature differentials across the sensor and enhances accuracy.

18 Claims, 5 Drawing Figures

DILATOMETER HOUSING

BACKGROUND OF THE INVENTION

1. Field of the Invention

This invention relates generally to dilatometers and, more particularly, to dilatometers having a hermetically sealed housing for both the sensor and the specimen. Such unitary housing permits operation of the dilatometer under vacuum or in a protective gas atmosphere and provides the operator with convenient access to the sensor for replacement, calibration or other necessary adjustments, as well as enabling him to quickly and easily replace specimens.

2. Description of the Prior Art

Dilatometers are analytical instruments that respond to the linear thermal expansion or contraction of solids. Typically, these instruments have a variable temperature furnace in which the test specimen rests between a flat surface on a stationary object and an opposing flat surface on a movable object, such as a ceramic pushrod, that extends outside the furnace. Temperature induced changes in the length of the specimen are transmitted through the rod to a mechanical, optical or electrical system for amplifying and measuring that change. These instruments can be used to make precise measurements of changes in length resulting from small temperature changes or to plot variations in the rate of linear expansion or contraction over a broad temperature range.

Among the least sophisticated dilatometers in common use are those in which the push rod is coupled to a dial gauge and the dilation of a specimen is read directly from that gauge. Such dial gauge dilatometers are simple to use and inexpensive, but generally are suitable only for low to moderate temperature applications that do not demand great precision.

U.S. Pat. No. 3,680,357 describes a far more precise type of dilatometer in which the dilation sensor is a linear variable differential transformer which translates specimen dilation into electrical signals that can readily be amplified and recorded. In such sensor, the core floats freely in the coil and each of these elements is separately supported at its ends by a pair of compound cantilevered springs. These springs permit independent and frictionless axial movement of the suspended element, but restrain radial or transverse movement. This independent and frictionless axial mobility of the core and coil facilitates calibration of the sensor and renders it extremely sensitive to minute changes in specimen length, thereby making possible exceptionally accurate measurements of thermally induced expansion or contraction.

Such dilatometers have been used for a wide variety of purposes. For example, those which have a single pushrod coupled to the core or coil of the linear variable differential dilatometer, as described in U.S. Pat. No. 3,805,589, are used in the steel industry to detect phase changes occurring when heat softened steel is cooled and to study the effect of different cooling rates on the physical properties of the finished product.

Such dilatometers which have separate pushrods coupled to the core and coil of the linear variable differential transformer, as described in U.S. Pat. No. 3,898,836, are widely used for making differential measurements on different specimens. These differential measurements are invaluable in studying the compatibility under changing temperature conditions of different materials which are bonded together or are in close contact; e.g., metal to glass, enamel to substrates, thin film deposits in microcircuits or metal or plastic fillings in natural teeth.

Dilatometers employing a linear variable differential transformer sensor also are available in which one or both of the core and coil are supported by linear ball bearings which permit low friction axial movement of the supported member while rigidly restricting axial movement, as illustrated in copending U.S. application Ser. No. 538,180, filed Oct. 3, 1983, which now is U.S. Pat. No. 4,521,119, issued June 4, 1985. Dilatometers having these sensors are particularly useful for making measurements on specimens that exhibit extremely large dimensional changes or for applications requiring the imposition of a constant force on the specimen.

Regardless of the dilation sensor that is employed, the temperature ranges that must be investigated for many applications are sufficiently high that it becomes necessary to protect both the specimen and the sensor from oxidation. It also is desirable for optimum accuracy of the sensor to minimize temperature differentials across the sensor and its adjacent metal supports and peripherals; e.g., the micrometer (which is used for calibration) and the sliding carriage (which accomodates specimens of differing length) that are illustrated in FIG. 1 of U.S. Pat. No. 3,680,357. As exemplified by FIG. 6 of that Patent, protection against oxidation and undesirable temperature differentials commonly is accomplished by placing the sensor, along with its adjacent metal supports and peripherals, within a metal box-like enclosure that is clamped with a hermetic seal on one side of a temperature stabilized radiation shield that is fixed to the instrument base. The push rod or rods extend through a small opening in the shield to abut the specimen or specimens within a communicating tubular enclosure that is similarly clamped and sealed on the other side of the shield and that extends into the furnace. Evacuation of the communicating enclosures minimizes the possibility of oxidation within the enclosures and, because it effectively blocks heat transfer to the sensor by both radiation and convection, measurements can be made with great precision at extremely high temperatures.

These enclosures do, however, make it difficult for the operator to visually observe the sensor, which is often desirable and is essential when using a dial gauge. It also hinders the operator when he must insert a specimen and calibrate the sensor, as the furnace first must be moved or opened to provide access to the tubular enclosure and both enclosures must then be unclamped and removed separately. This often is awkward and is potentially dangerous when the furnace and tubular enclosure are still hot from a previous measurement. The time and effort required to change sensors also effectively precludes the use of a single instrument for multiple applications that require the use of different specialized sensors.

It is an object of this invention to provide a dilatometer having an improved hermetically sealed housing for the dilatometer sensor, pushrod and specimen holder, which includes an elongated protective tube enclosure for the portion of the specimen holder that is inserted in an electric tube furnace. It is a specific object of this invention to provide such housing which is light weight and compact and which can easily and quickly be withdrawn as a unit from a stationary or unopened furnace to facilitate the rapid installation of similar housings having specialized sensors or tubular enclosures designed for different applications. It also is a specific object of this invention to provide such housing from which the sensor, push rod and specimen holder can be quickly removed as a unit for changing specimens, without the necessity of withdrawing the protective tube from the furnace or realigning it after reinsertion. Another specific object is to protect the contents of such housing from oxidation by evacuating the housing and by providing a flow of protective gas across the specimen. A further object of this invention is to provide such dilatometer having an improved dilation sensor design which minimizes temperature differentials across that sensor.

It has been found that these objects and other advantages, which will be apparent from this specification, are achieved by the invention described below.

Broadly, my invention is a compact unitary housing for a dilatometer sensor, pushrod and specimen holder which protects its contents from furnace heat, which conveniently can be handled as a unit and from which these contents can easily be withdrawn as a unit.

One aspect of this invention is such housing for a dilation sensor, pushrod and specimen holder of a dilatometer comprising (a) a sleeve for encircling said sensor, (b) a cover closing one end of said sleeve, (c) a sensor attachment beam secured to said cover and extending into said sleeve, (d) a ring shaped plate closing the other end of said sleeve and being demountably held to said attachment beam to lock said cover to said sleeve, and (e) a protective tube for said specimen holder, said protective tube being closed at one end and being coupled at its open end to said plate distal to said sleeve, the aperture of said plate and the bore of said protective tube being aligned.

A specific application of this aspect of the invention is the use of such housing in an encased dilatometer comprising (a) a dilation sensor mounted on an elongated attachment beam, (b) a tubular fixed specimen holder having an open end and a closed end that is internally adapted to abut a flat surface of a specimen, said specimen holder being held adjacent its open end by a clamp mounted on said attachment beam, (c) a movable pushrod that is coupled at one end to said sensor and at the other end is adapted to abut a second parallel flat surface on said specimen, said pushrod extending into the open end of said tubular fixed specimen holder, (d) a tubular sleeve encircling said attachment beam, sensor and clamp, (e) a cover closing and hermetically sealing the end of said sleeve distal to said clamp, said cover being attached to an end of said attachment beam, (f) a ring shaped plate closing and hermetically sealing the other end of said sleeve and being demountably coupled to the other end of said attachment beam to adjustably lock said cover to said sleeve, said plate containing a vacuum port and having a connecting tube extending from the rim of its aperture distal to said sleeve and terminating in a first flange at its open end and (g) a protective tube having a closed end and a second flange at its open end which is demountably clamped and hermetically sealed to said first flange, said specimen holder extending loosely through said aperture and connecting tube into the open end of said protective tube.

Another aspect of this invention is a compact design for a dilation sensor for a dilatometer that minimizes temperature differentials across the sensor and that advantageously is used in the aforementioned housing. This improved sensor comprises a linear variable differential transformer having a core and coil that are independently axially movable and a calibrating micrometer, said micrometer being positioned adjacent to and abreast of said linear variable differential transformer and bearing on a lateral extension of said core or coil.

DESCRIPTION OF THE PREFERRED EMBODIMENTS

Figure 1:
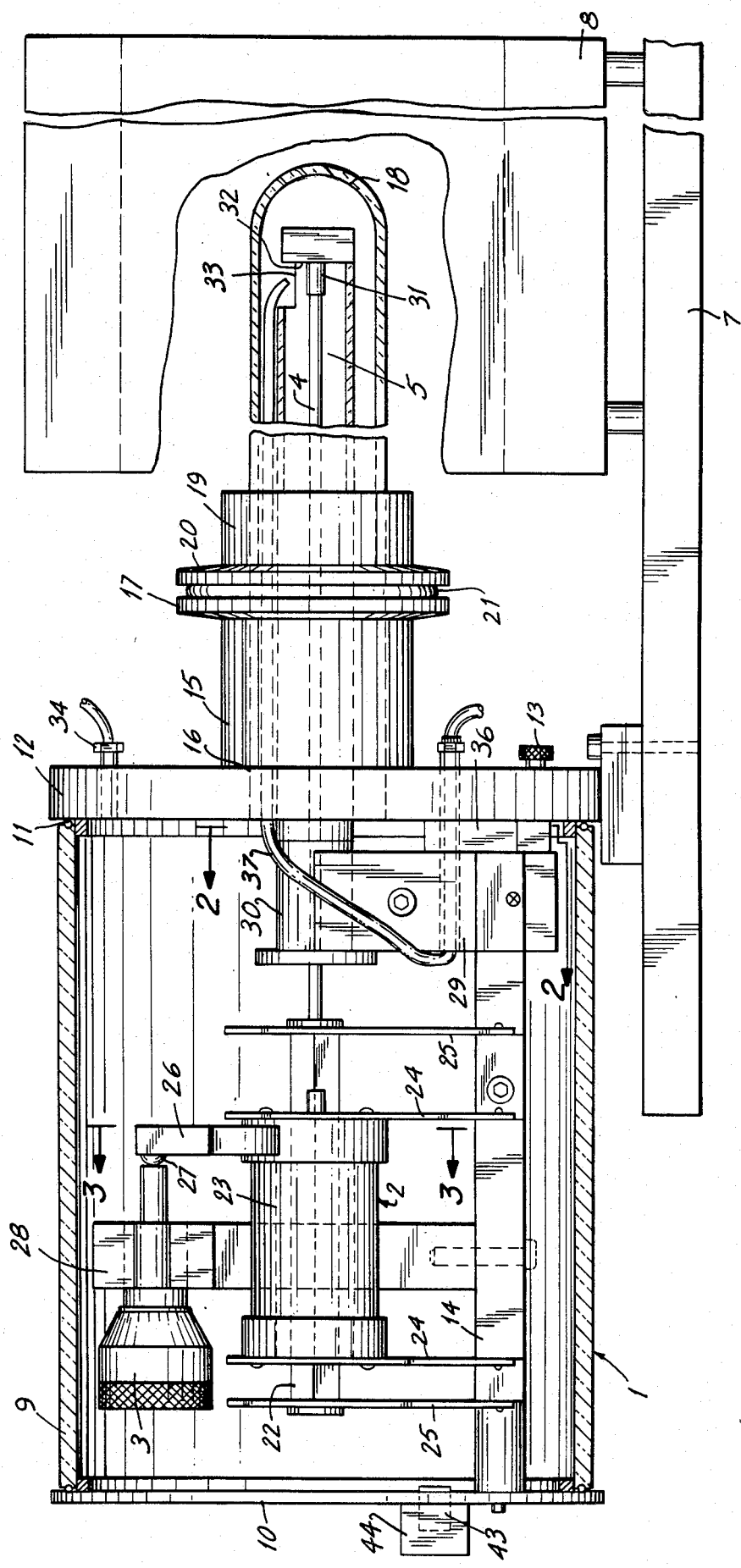
FIG. 1 is a side elevation, partially cut away, of a dilatometer of this invention having the dilation sensor and specimen holder within a hermetically sealed housing.

FIG. 1 illustrates a preferred embodiment of this invention in which a unitary hermetically sealed housing 1 encloses a linear variable differential transformer dilation sensor 2, a calibrating micrometer 3, a pushrod 4 and a specimen holder 5, as well as their support systems, which will be described in detail below. Housing 1 is attached to mounting block 6, which can be clamped or bolted (as illustrated) to instrument base 7, which also supports electric tube furnace 8.

Figure 5:
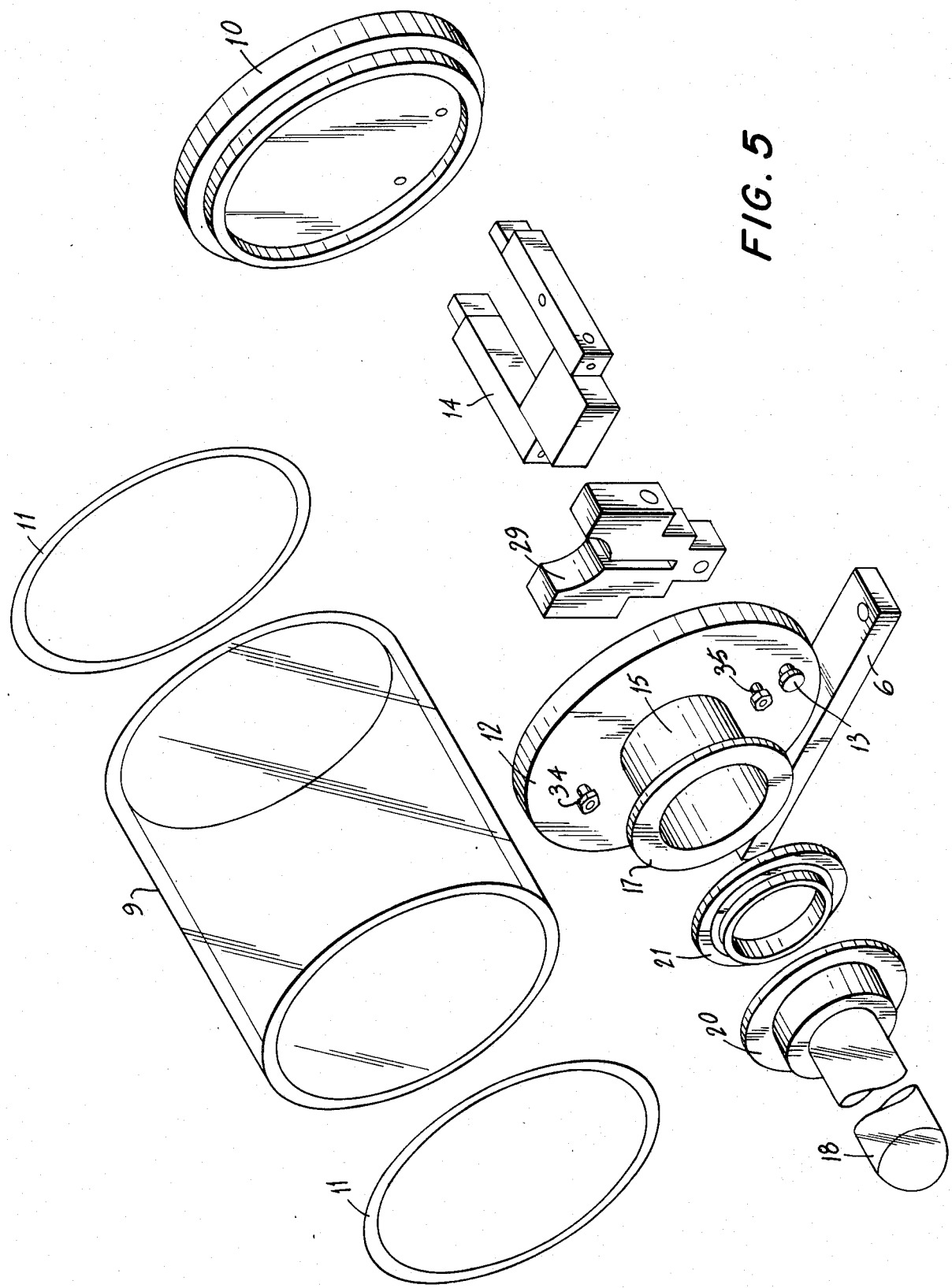
FIG. 5 is a partial exploded perspective view of the housing of FIG. 1 with parts omitted for clarity

As shown in FIGS. 1 and 5, housing 1 has a cylindrical sleeve 9 that encircles sensor 2 and portions of pushrod 4 and specimen holder 5. Sleeve 9 may be made of metal, but preferably is of a transparent material, such as glass or polycarbonate resin, which permits the visual observation of the sensor that is desirable when employing the illustrated sensor and is essential when employing a dial gauge sensor. The left end of sleeve 9 is closed by cover 10 and sealed by a rubber O-ring 11 which is positioned between cover 10 and the edge of the sleeve 9 wall. The right end of sleeve 9 is similarly closed and sealed by ring shaped plate 12 and another O-ring 11. Threaded fastener 13 passes through an opening (not shown) in plate 12 and engages a threaded hole (not shown) in attachment beam 14, which extends through sleeve 9 and is bolted to cover 10. Tightening fastener 13 presses cover 10 and plate 12 against O-rings 11 and insures a hermetic seal with sleeve 9.

Cover 10 contains an electrical feedthrough 43 for the wires (not shown) from the linear variable differential transformer dilation sensor 2 and from a thermocouple (not shown) that advantageously is attached to the specimen 31. The outer portion of feedthrough 43 is protected by shell 44 which is attached to the outer surface of cover 10.

Ring shaped plate 12 contains a vacuum port 34 for evacuating housing 1 and an inlet port which will be discussed below. It also has a high melting metal connecting tube 15 extending outward from the rim of its oriface 16 and terminating in a flange 17. Protective tube 18, which for high temperature applications advantageously is made of alumina or fused silica, has a single open end that is bonded to a high melting metal ring 19 having a flange 20. Flanges 17 and 20 are held together by a clamp (not shown) to align the bore of protective tube 18 with the similar diameter orifaces in plate 12 and connecting tube 15. A hermetic seal is provided by intermediately positioned O-ring 21 that is made of a temperature resistant material such as a polyperfluoroethylene resin. Alternately, the protective tube can be demountably held and sealed to the ring shaped plate by threaded pipe fittings.

The lower portion of plate 12 is attached to mounting block 6, which is held by two bolts to instrument base 7. Housing 1 and its entire contents may be removed as a unit simply by unfastening these bolts and sliding the housing to the left until the tip of the protective tube 18 clears furnace 8.

Figure 3:
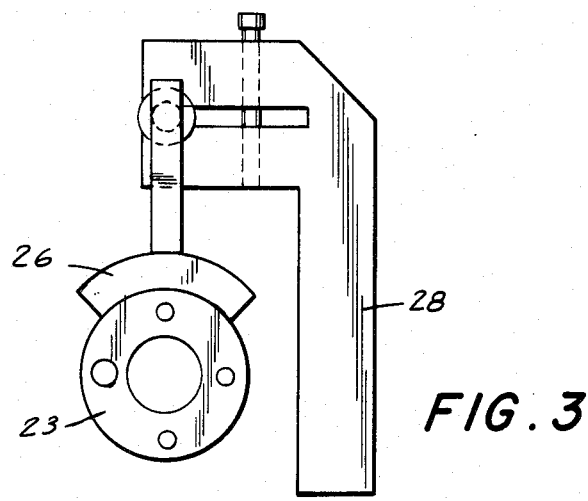
FIG. 3 is a partial cross section, along line B—B of FIG. 1, showing the calibrating micrometer bracket within the housing.

The dilation sensor illustrated in FIG. 1 is a particularly preferred modification of the conventional linear variable differential transformer sensor described in U.S. Pat. No. 3,680,357. It has a core 22 which is supported at its ends by a pair of compound cantilevered flat springs 25 which are mounted on attachment beam 14. Core 22 floats freely in the coil 23, which also is supported at its ends by a separate but similar pair of compound cantilevered flat springs 24 that are mounted on attachment beam 14. These springs permit independent and frictionless axial movement of the suspended elements, but restrain radial or transverse movement. Sensor 2 differs from that of the aforementioned Patent primarily in that the calibrating micrometer 3, along with micrometer bracket 28 which is attached to beam 14, is located close to and abreast of coil 23, rather than these elements being in tandem. As illustrated in FIGS. 1 and 3, bracket 28 clamps the neck of micrometer 3 (not shown in FIG. 3) and permits its stem to bear on a hemispherical anvil 27 on a lateral extension 26 of coil 23. Turning the micrometer causes a precisely measured movement of the coil which is correlated with electrical output in the conventional manner.

The positioning of the micrometer and bracket, as illustrated, shortens the assembly and, by reducing the temperature differentials which result from different portions of the assembly being located at different distances from the furnace, minimizes the effect of these differentials on the electrical output of the linear variable differential transformer. This positioning of the micrometer abreast of the coil is advantageously employed on any one or two pushrod dilation sensor that utilizes a linear variable differential transformer, regardless of whether the core or coil are supported by frictionless compound cantilevered springs, low friction linear ball bearings or simple slides, and it is especially preferred to use same in the unitary dilatometer housing of this invention, as illustrated in FIGS. 1 and 5. For certain applications, however, it may be desirable to recalibrate the sensor during a measurement and this inaccessable positioning of the micrometer would make that impossible. In such case, it is preferred to retain the tandem arrangement of micrometer and linear variable differential transformer shown by U.S. Pat. No. 3,680,357. Such arrangement can be accomodated by mounting the micrometer so that its neck is held in a hole through cover 10 with its body outside housing 1 and only its stem extending inside.

Returning to FIG. 1, specimen holder 5 is a tube, preferably made of alumina or fused silica, which is bonded at its open end to a flanged high melting metal ring 30 and has a flat ground surface 32 on the inner surface of its closed end. Push rod 4, which is coupled to core 22 of sensor 2, extends into the open end of specimen holder 5 and abuts a specimen 31 resting against flat ground surface 32. Specimen holder 5, which also has an opening 33 in its wall to facilitate specimen changes, is held adjacent its open end by clamp 29 and extends through ring shaped plate 12 into protective tube 18. Specimen 31 can be swept by an inert or reducing gas, such as argon or hydrogen, by passing such gas through inlet port 35, fluid fitting 36 and conduit 37, which extends into protective tube 18 and discharges the gas into opening 33 in the wall of specimen holder 5. Advantageously, at least that portion of conduit 37 which is in protective tube 18 is made of a heat resistant material such as alumina or fused silica.

Figure 2:
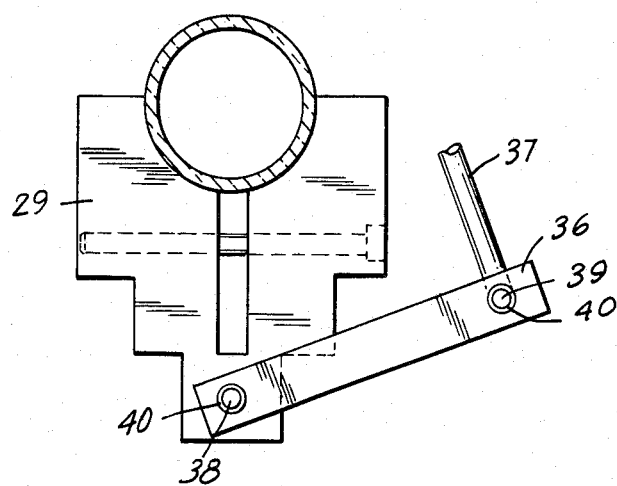
FIG. 2 is a partial cross section, along line A—A of FIG. 1, showing the specimen holder clamp and inert gas fitting and conduit within the housing.

FIGS. 1 and 2 most clearly show specimen holder clamp 29, which is bolted to attachment beam 14, and fluid fitting 36, which is bolted to clamp 29. Screw 13 passes through plate 12 (both shown only in FIG. 1) and through hole 38 in fitting 36 and clamp 29 before engaging the end of attachment beam 14. The oriface 39 in fitting 36 is aligned with inlet port 35 in plate 12 and is encircled by a rubber O-ring 40 that is retained in a matching groove (not shown) in fitting 36. Hole 38 in fitting 36 is similarly encircled by an O-ring 40. When screw 13 is tightened into attachment beam 14, fitting 36 is pressed tightly against plate 12 and O-rings 40 provide a hermetic seal.

Figure 4:
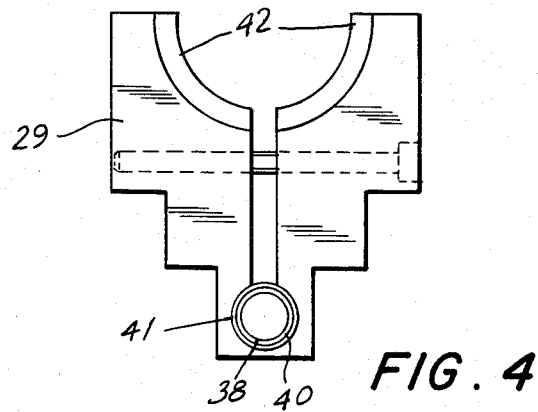
FIG. 4 is an alternate embodiment of the specimen holder clamp of FIG. 2.

FIG. 4 shows an alternative to the embodiment of FIG. 2 which is useful when gas inlet port 35 (not shown in this drawing) is absent or closed. the fluid fitting is replaced with an equal thickness cylindrical adapter 41 which similarly retains a sealing O-ring encircling its oriface through which screw 13 passes. Specimen holder clamp 29 here is shown with plastic pads 42 in its jaws which facilitate holding specimen holders which are not bonded to a metal ring.

As noted above, housing 1, along with its entire contents, can be removed simply by detaching mounting block 6 from instrument base 7 and withdrawing protective tube 18 from furnace 8, thus facilitating use of the furnace for multiple dilatometer applications that may require different sensors, pushrod or rods, specimen holders or protective tubes. If, however, the operator merely wishes to change specimens, screw 13 can be disengaged, which permits cover 10 and attachment beam 14 and the entire contents of housing 1 to be removed as a unit, without the necessity of withdrawing and subsequently realigning the protective tube with the furnace or of breaking and subsequently reconnecting any external vacuum or gas connections. After the specimen has been changed and the unit replaced, housing 1 is completely sealed and the inert gas connection completed simply by tightening screw 13, thus facilitating rapid repetitious measurements.

It will, of course, be understood that various additions and modifications may be made in the embodiments of this invention described above without departing from the spirit and scope of the invention as defined in the claims below.

The embodiments of the invention in which an exclusive property or privilege is claimed are defined as follows:

1. Housing for supporting a dilation sensor, pushrod and specimen holder of a dilatometer comprising
   (a) a sleeve for encircling said sensor, said sleeve having two opening ends,
   (b) a cover closing one said open sleeve end,
   (c) a sensor attachment beam secured to said cover and extending into said sleeve,
   (d) a ring shaped plate closing the other said open sleeve end, said plate having a circular aperture and being demountably held to said attachment beam to lock said cover and said plate to said sleeve, and
   (e) a protective tube having a bore for receiving said speciment holder, said protective tube being closed at one end and being coupled at an opposite open end to a side of said plate opposite said sleeve, said plate aperture and said protective tube bore being aligned.

2. Housing of claim 1 wherein said cover and said plate are hermetically sealed to said sleeve and said protective tube is demountably coupled and hermetically sealed to said plate.

3. Housing of claim 2 wherein said sleeve is tubular and O-ring seals are located between each of said cover and plate and said tubular sleeve and between said plate and said protective tube.

4. Housing of claim 2 including a clamp mounted on said attachment beam for holding an end of an elongated specimen holder that extends through the aperture of said plate into said protective tube.

5. Housing of claim 2 wherein said plate contains a vacuum port and a protective gas inlet port, said inlet port being connected within said sleeve to a fluid conduit extending through the aperture of said plate and discharging adjacent the closed end of said protective tube.

6. Housing of claim 5 wherein said conduit is connected to said inlet port through a fluid fitting which is mounted on said attachment beam and which is seated against said inlet port when said ring shaped plate is coupled to said attachment beam.

7. Housing of claim 6 including an O-ring seal positioned between said fluid fitting and said inlet port, said O-ring being retained in a circular depression in said fitting sourrounding its aperture.

8. Housing of claim 2 wherien said ring shaped plate is demountably coupled to said attachment beam be a threaded fastener passing through said plate and engaging said beam.

9. Encased dilatometer comprising
   (a) a dilation sensor mounted on an elongated attachment beam,
   (b) a tubular fixed specimen holder having an open end and a closed end that is internally adapted to abut a flat surface of a specimen, said specimen holder being held adjacent its open end by a clamp mounted on said attachment beam,
   (c) a movable pushrod that is coupled at one end to said sensor and at the outer end is adapted to abut a second parallel flat surface on said specimen, said pushrod extending into the open end of said tubular fixed specimen holder,
   (d) a tubular sleeve encircling said attachment beam, sensor and clamp,
   (e) a cover closing and hermetically sealing a first end of said sleeve distal to said clamp, said cover being attached to an end of said attachment beam,
   (f) a ring shaped plate closing and hermetically sealing a second end of said sleeve and being demountably coupled to an opposite end of said attachment beam to adjustably lock said cover to said sleeve and to permit said cover and sensor attachment beam to be removed as a unit, said plate containing a vacuum port and having a connecting tube extending for a rim of a circular aperture of said plate on a side of said plate opposite said connecting tube terminating in a first flange at an open end and said sleeve,
   (g) a protective tube having open and closed ends and a second flange at said open end which is demountably clamped and hermetically sealed to said first flange, said specimen holder extending loosely through said aperture and connecting tube into the open end of sid protective tube.

10. Dilatometer of claim 9 wherein said specimen holder has an opening in its wall adjacent said closed end of said holder which provides access to a specimen.

11. Dilatometer of claim 9 wherein said ring shaped plate contains a protective gas inlet port which is connected within said sleeve to a conduit extending through the aperture of said ring shaped plate and discharging adjacent the closed end of said specimen holder.

12. Dilatometer of claim 11 wherein said conduit is positioned outside said specimen holder and discharges into said specimen holder wall opening.

13. Dilatometer of claim 12 wherein said conduit is connected to said inlet port through a fluid fitting which is mounted on said attachment beam and which is seated against said inlet port when said ring shaped plate is coupled to said attachment beam, the orifice of said fitting being sealed to said inlet port by an intermediately positioned O-ring which is retained in a circular depression in said fitting surrounding said orifice.

14. Dilatometer of claim 9 wherein said tubular sleeve is a transparent material.

15. Dilatometer of claim 14 wherein said dilation sensor is a dial gauge.

16. Dilatometer of claim 9 wherein said dilation sensor is a linear variable differential transformer having a core and coil that are independently axially movable.

17. Dilatometer of claim 16 wherein a calibrating micrometer is held by and extends through said cover, said micrometer being positioned in tandem with said linear variable differential transformer and bearing on an axial extension of one of said core and coil.

18. Dilatometer of claim 9 including an electrical feedthrough in said cover and a shell protecting said feedthrough which is held to said cover on a side of cover opposite said sleeve.

* * * * *